US007730784B2

(12) United States Patent
Georgeson et al.

(10) Patent No.: US 7,730,784 B2
(45) Date of Patent: Jun. 8, 2010

(54) ULTRASONIC METHOD TO VERIFY THE INTERFERENCE FIT OF FASTENERS

(75) Inventors: Gary E. Georgeson, Federal Way, WA (US); James H. Lee, Ravensdale, WA (US); Karl E. Nelson, Shoreline, WA (US)

(73) Assignee: The Boeing Company, Chicago, IL (US)

( * ) Notice: Subject to any disclaimer, the term of this patent is extended or adjusted under 35 U.S.C. 154(b) by 347 days.

(21) Appl. No.: 11/833,826

(22) Filed: Aug. 3, 2007

(65) Prior Publication Data

US 2009/0031811 A1 Feb. 5, 2009

(51) Int. Cl.
*G01N 29/18* (2006.01)
(52) U.S. Cl. ............................. 73/579; 73/597; 73/598; 73/602
(58) Field of Classification Search .................. 73/597, 73/598, 761, 801, 802; 29/407.07, 705
See application file for complete search history.

(56) References Cited

U.S. PATENT DOCUMENTS

| 4,062,227 | A | | 12/1977 | Heyman | |
| 4,702,658 | A | * | 10/1987 | Salter | 411/426 |
| 5,280,725 | A | * | 1/1994 | Stengel | 73/761 |
| 5,291,789 | A | * | 3/1994 | Walton | 73/761 |
| 5,297,435 | A | | 3/1994 | Papazian | |
| 6,253,615 | B1 | * | 7/2001 | Simmonds et al. | 73/579 |
| 6,964,362 | B2 | * | 11/2005 | Shkolnikov et al. | 227/130 |
| 7,528,598 | B2 | * | 5/2009 | Goldfine et al. | 324/240 |
| 2001/0034009 | A1 | | 10/2001 | Lang et al. | |
| 2005/0173489 | A1 | * | 8/2005 | Shkolnikov et al. | 227/130 |

FOREIGN PATENT DOCUMENTS

| AU | 617770 | | 12/1991 |
| JP | 408258169 A | * | 10/1996 |

OTHER PUBLICATIONS

Koshti, "Simulation of Ultrasonic Preload Measurement on a Bolt in an Interference Fit Joint", Smart Nondestructive Evaluation for Health Monitoring of Structural and Biological Systems, Mar. 2002, Newport Beach, USA, Proceedings of SPIE, vol. 4702, pp. 423-437.
PCT Intl Search Report and Written Opinion for application No. PCT/US2008/072021, dated May 18, 2009, 14 pgs.

* cited by examiner

*Primary Examiner*—J M Saint Surin
(74) *Attorney, Agent, or Firm*—Lee & Hayes, PLLC (57) ABSTRACT

Embodiments of techniques to verify the interference fit of fasteners are disclosed. In one embodiment, a method includes aligning a probe proximate a fastener, the fastener being disposed within a material. A dynamic stress signal is generated from the probe using a low frequency transducer, and the dynamic stress signal is interrogated after it passes between the fastener and the material. An interference fit is then determined based on the interrogated dynamic stress signal.

18 Claims, 7 Drawing Sheets

ULTRASONIC METHOD TO VERIFY THE INTERFERENCE FIT OF FASTENERS

TECHNICAL FIELD

The present disclosure teaches ultrasonic measurement techniques, and more specifically, methods for ultrasonically measuring and verifying an interference fit of fasteners.

BACKGROUND

Recent estimations indicate that, on the average, each aircraft in the U.S. commercial aircraft fleet receives a lightning discharge about once each year. The aircraft generally experiences the lightning discharge when flying through a heavily charged portion of a cloud. In such cases, the discharge generally originates at the aircraft and extends outwardly from the aircraft. While the discharge is occurring, it generally moves from the nose of the aircraft and onto a plurality of skin panel portions of the aircraft as it moves through the charged region. The discharge may also attach to wing tips and/or edges of wing control surfaces (e.g., ailerons) during the discharge. The discharge then generally leaves the aircraft structure through the empennage. Since commercial aircraft contain relatively large amounts of fuel, and also generally include sensitive electronic equipment such as navigational computers and communications equipment that may be damaged by a lightning discharge, commercial aircraft are required to comply with a comprehensive set of certification procedures in order to verify that the aircraft is sufficiently protected from the potentially damaging effects of a lightning discharge.

Today's aircraft are being designed and built with greater percentages of composite material. Although composites are lighter and may have better mechanical and fatigue properties than traditional aluminum, they are less electrically conductive, and have poor electromagnetic shielding, causing poor current dissipation when lightning strikes the aircraft. Without an adequate conductive path, arcing and hot spots can occur that may char, delaminate and/or penetrate an aircraft's composite skin, and may reduce the load-bearing characteristics of the aircraft structure. For example, lightning may attach to a fastener and then flow though the fastener into a sub-structure below the surface (or skin) of the aircraft. The low electrical conducting capacity of composite materials may increase the likelihood that sub-structures may be adversely affected by the lightning strike, particularly when lightning attaches to a fastener, if additional safety techniques are not implemented.

Therefore, techniques to improve an airframe's tolerance to lightning strikes, particularly when lightning attaches to aircraft fasteners, have utility and may improve the economy and/or safety of air transit.

SUMMARY

Embodiments of techniques to verify the interference fit of fasteners are disclosed. Such techniques may be used to inspect and verify an interference fit between an electrically-conductive fastener and an electrically-conductive layer of a Lightning Strike Protection (LSP) system of a structure, including a fiber-reinforced composite structure. Techniques in accordance with the present disclosure may advantageously ensure that an electrically-conductive path exists between the fastener and the LSP system so that an electrical charge may be properly conducted through the structure, thereby reducing or eliminating damage that might otherwise occur to the structure.

In one embodiment, a method includes aligning a probe proximate a fastener, the fastener being disposed within a material. A dynamic stress signal is generated from the probe using a low frequency transducer, and the dynamic stress signal is interrogated after it passes between the fastener and the material. An interference fit is then determined based on the interrogated dynamic stress signal.

In another embodiment, a method for determining an interference fit of a fastener includes transmitting a low frequency stress wave through a first portion of a structure, the structure including a material secured with a fastener, and monitoring an ultrasonic signal transmitted through a second portion of the structure. The second portion is separated from the first portion by an interference portion defined between the fastener and the material. The method further includes measuring a phase shift from the ultrasonic signal, and determining an interference fit from the measured phase shift.

In a further embodiment, a method for determining an interference fit of a fastener includes aligning a probe to a fastener and activating the probe, the probe transmitting low frequency stress waves into a first portion of a structure, and measuring the stress waves with an ultrasonic signal at a second portion of the structure. The first and second portions of the structure are separated by an interference between a fastener and a material proximate the fastener. The method further includes calculating an interference fit between the fastener and the material from the measured stress waves, and determining if the interference fit is within a threshold range.

The features, functions, and advantages can be achieved independently in various embodiments of the present disclosure or may be combined in yet other embodiments.

BRIEF DESCRIPTION OF THE DRAWINGS

Embodiments of techniques in accordance with the present disclosure are described in detail below with reference to the following drawings.

DETAILED DESCRIPTION

Overview

Techniques to verify the interference fit of fasteners are described herein. Many specific details of certain embodiments of the disclosure are set forth in the following description and in FIGS. 1 through 7 to provide a thorough understanding of such embodiments. One skilled in the art, however, will understand that the present disclosure may have additional embodiments, or that the present disclosure may be practiced without several of the details described in the following description.

Aircraft employ lightning strike protection (LSP) systems to protect the aircraft from damage when it is struck by lightning or otherwise undergoes an electrical charge. One approach is to incorporate a layer of conductive metal in the aircraft skin to evenly distribute electrical energy from a lightning strike across a large surface area, and thus avoid concentrations of energy that may cause burning, material failure, or other damage to the aircraft. Often, fasteners that connect the aircraft skin to internal structures are protected from lighting strikes when the fasteners are recessed below the conductive layer within the skin of the aircraft. The fasteners are typically covered with a non-conductive material to further conceal the fasteners from direct lightning strikes. Despite these precautions, lightning may occasionally attach itself to a fastener and flow down the fastener shaft. In such an instance, it is desirable to effectively draw the electrical energy through the aircraft skin and spar in an efficient manner, and thus avoid heating and/or damage to the fastener or surrounding material. In order for the electrical energy to be efficiently drawn from the fastener, the fastener advantageously has a tight interference fit with the surrounding material.

The interference fit of a fastener relates to a measure of closeness of the fit between the fastener shank and the surrounding material forming a fastener hold. For example, the fastener hole may be drilled though the material at a diameter of 9.5 mm for a bolt with 10 mm diameter, thus creating a positive interference fit of 0.5 mm. In such an instance, the fastener may be inserted into the hole by compressing the surrounding material in a direction perpendicular to the axis of the fastener shank.

While not intending to be bound by theory, it is believed that microscopic gaps typically exist between the fastener shank and the fastener hole. These gaps cause the current flow between the fastener shank and the material to be focused at the points where contact is made. By providing an interference fit, and thus compressing the surrounding material with the fastener shank, it is believed that the microscopic gaps are minimized resulting in increased electrical contact area and thus increased conductive properties between the fastener and the surrounding material. Increased conductivity reduces or eliminates any negative effect of lightning attaching to the fastener because the electrical energy may be dispersed into the skin or spar if the interference fit of the fastener is within a design threshold range.

To ensure the interference fit is in conformance with design requirements, methods to verify the interference fit are necessary. For example, aircraft manufacturing variables can impede consistent fit between the fastener and the fastener hole, such as operator error, slightly oversized drill bits, dull drill bits, and undersized fasteners. Methods are needed to confirm the degree of interference fit after the fastener is installed, and in some cases, after extended use of an aircraft to ensure the interference fit remains within the design threshold range.

Illustrative Interference Fit Testing Apparatus

Figure 1:
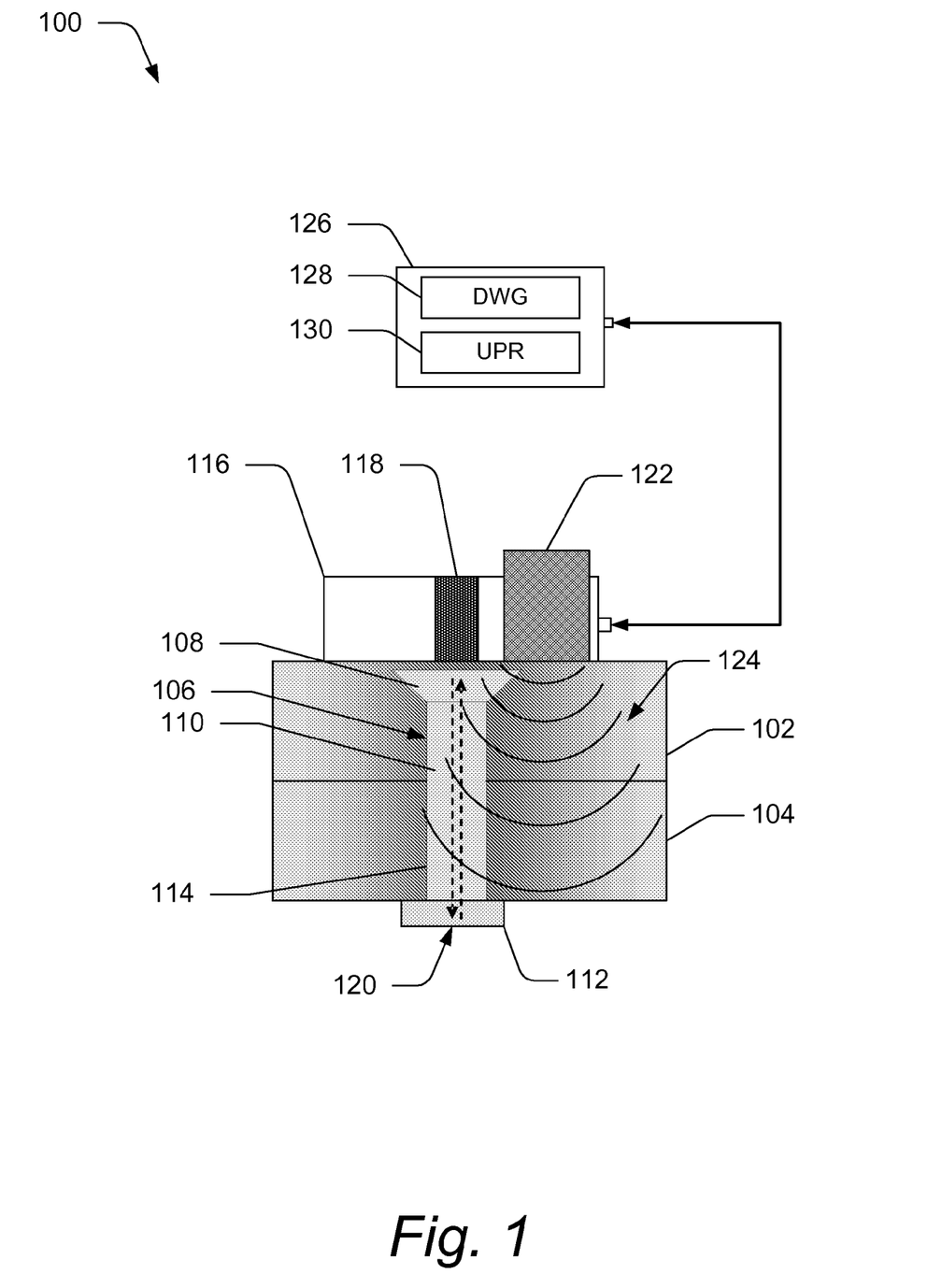
FIG. 1 is a cross-sectional view of an apparatus configured to verify an interference fit of a fastener in accordance with an embodiment of the disclosure.

FIG. 1 is a cross-sectional view of an apparatus configured to verify an interference fit of a fastener in accordance with an embodiment of the disclosure. An environment 100 includes a first material 102 and a second material 104 securably coupled by a fastener 106 disposed through a fastener hole 114. The fastener 106 includes a head 108, a shank 110, and a nut 112. Tightening the nut 112 on the shank 110 causes the fastener head 108 and the nut 112 to exert compressive forces on the first and second materials 102, 104. In addition, the fastener shank 110 may create radial stresses in the first material 102 and second material 104 when the environment 100 includes an interference fit, such that the fastener hole 114 has a smaller diameter than the diameter of the shank 110. The radial stresses in the first and second materials 102, 104 may be highest at the interface between the fastener 106 and the materials 102, 104, and typically reduce in magnitude as the distance from the fastener 106 increases. Detection and measurement of the radial stresses may provide information about the interference fit, and thus allow measurement of the interference fit to determine if it is in conformance with a design threshold range. This information may indicate that the fastener installation that is subjected to a lightning strike will provide adequate current dissipation into the surrounding material, provided the material can conduct electricity. For example, in the embodiment shown in FIG. 1, either one or both of the first and second materials 102, 104 may be electrically conductive, or alternately, may include an electrically-conductive layer of a Lightning Strike Protection (LSP) system.

With continued reference to FIG. 1, the environment includes a fastener interference fit (FIF) probe 116. The FIF probe 116 includes a high frequency (HF) ultrasonic testing (UT) transducer 118. In some embodiments, high frequency may be defined as ranging between about 1 MHz to 10 MHz. The HFUT transducer 118 produces ultrasonic signals 120 traveling substantially parallel to the axis of the fastener shank 106. In addition, the FIF probe 116 also includes a low frequency (LF) transducer 122 for creating dynamic stress waves 124. In some embodiments, low frequency may be defined as ranging between about 10 kHz to 250 kHz. The LF transducer 122 may be mounted adjacent to the HF transducer 118, such that the HF transducer 118 is proximate the fastener 106 and the LF transducer 122 is proximate the first material 102. In some instances, the LF transducer 122 may be a ring transducer configured to produce uniform stress waves 124 around the fastener 106.

In embodiments, ultrasonic waves may be between approximately 10 kHz to 75 MHz, while ultrasonic waves are typically above 10 MHz for specialized applications such as for thin or near surface inspection (or measurements). Although the present disclosure includes ultrasonic waves, other waves, such as microwaves may be used to measure the interference fit of a fastener. For example, measurements of the shifts in the velocity or phase of microwaves could be used to determine the interference fit of a fastener as described herein. Generally speaking, the speed of a so-called 'thermal wave' is affected by stress as thermal diffusivity changes due to the stress state. Thus, embodiments may include flash thermography (thermal waves), particularly for thinner structures. An example of such a flash infrared system is the EchoTherm® made by TWI (Thermal Wave Imaging) of Ferndale, Mich. In some instances, the dissipation of the heat as measured by the temperature at the surface may be different for a higher stressed (high interference) area around a fastener as compared to a lower stressed (low interference) area. In still further embodiments, non-contact laser-based ultrasonics may be used instead of having a transducer that contacts the surface to send and receive the signals.

A stress state of the fastener 106 can be used to validate the interference fit at the fastener/structure interface. In operation, the FIF probe 116 measures the stress state of the installed fastener 106 and infers the hoop stresses at the interface between the fastener 106 and the surrounding materials 102, 104. The dynamic stress waves 124 may be applied to the area around the fastener 106 using the LF transducer 122. The HFUT transducer 118 may interrogate the fastener 106 with the ultrasonic signals 120. A resulting measured phase shift of the ultrasonic signals 120 may be correlated to the radial stresses on the fastener 100, and therefore provides a measurement that is characteristic of the interference fit. This approach may work with thicker structures or structures where the skin and substructure are not physically bonded.

In some embodiments, the FIF probe 116 is in communication with a controller 126. The controller 126 may include a dynamic wave generator (DWG) 128 and an ultrasonic pulse receiver (UPR) 130 having signal analysis capabilities, however other configurations are contemplated. The dynamic wave generator 128 may provide wave generation information to the HFUT transducer 118 and/or the LF transducer 122. The ultrasonic pulser receiver 130 may receive signals from the HFUT transducer 118 indicative of the ultrasonic signals 120. As described above, the ultrasonic signals 120 may then be analyzed to determine information about the interference fit between the fastener 106 and the materials 102, 104. For example, the controller 126 may be a computer, server, or other computing device including one or more processors operably connected to storage media having modules to perform the techniques disclosed herein, such as the functions performed by the dynamic wave generator 128 and the ultrasonic pulser receiver 130.

In some embodiments in accordance with the present disclosure, phase-locked non-linear ultrasonic testing (UT) is used to measure the interference fit. The phase-locked non-linear UT may be conducted with any suitable equipment, such as the UT equipment manufactured by Luna Innovations Incorporated of Roanoke, Virginia. In a particular embodiment, the phase-locked non-linear UT uses ultrasonic beam mixing to measure phase shifts that are sensitive to small changes in material properties, including stress states. A low frequency applied dynamic stress may be generated by a first source while a second source sends and receives a higher frequency signal. The HF ultrasonic signals 120 undergo a frequency shift caused by the LF stress waves 124. Amplitude of the frequency shift depends on a third order elastic constant (non-linear) that is affected by the stress state. One illustrative system that uses phase-locked non-linear UT is the Phlite® ultrasonic system of Luna Innovations Inc.

Figure 2:
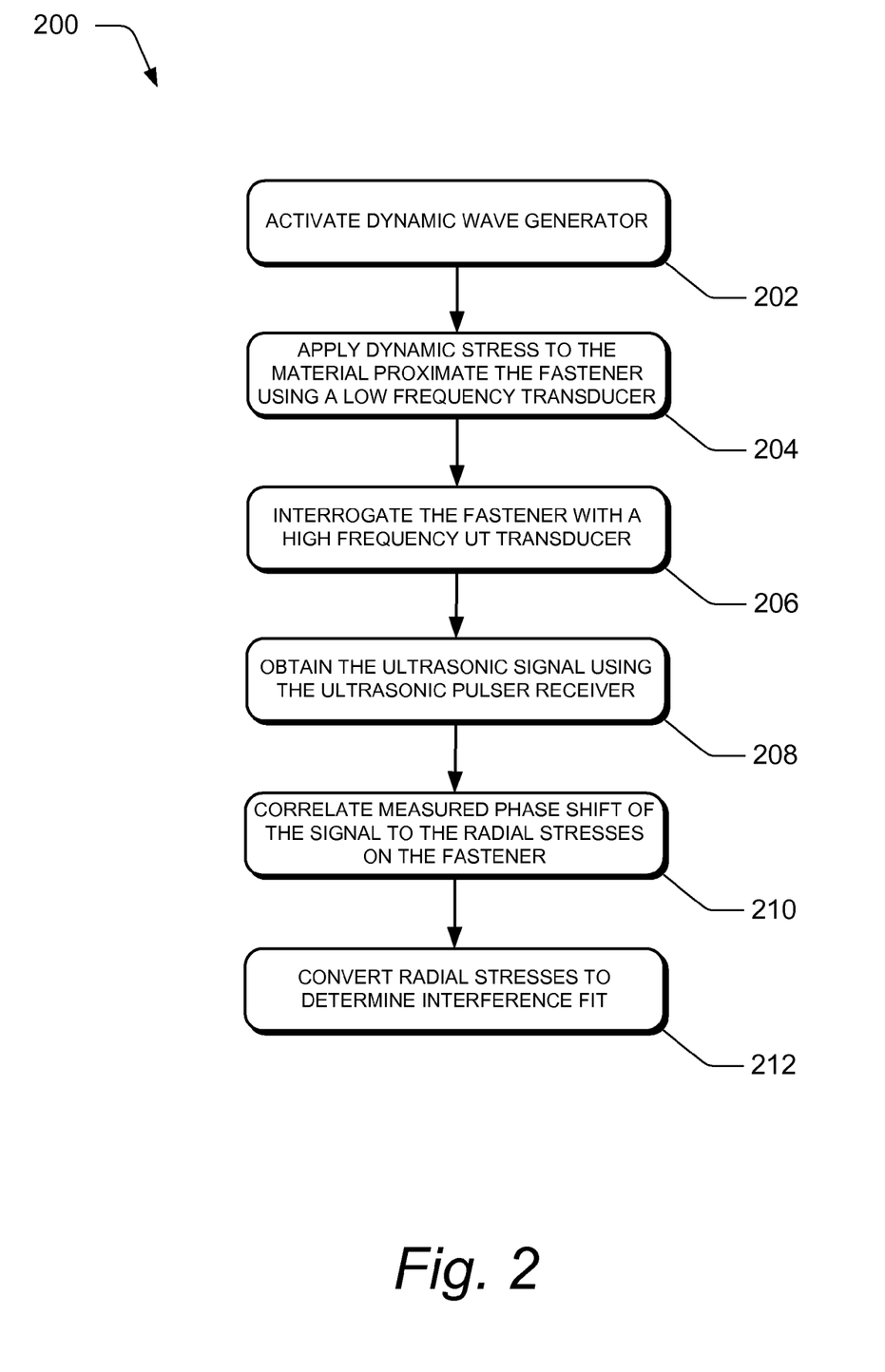
FIG. 2 is a flow diagram of a process for verifying the interference fit of a fastener in accordance with an embodiment of the disclosure.

FIG. 2 is a flow diagram of a process 200 for verifying the interference fit of a fastener in accordance with an embodiment of the disclosure. The process 200 is illustrated as a collection of blocks in a logical flow graph, which represents a sequence of operations that can be implemented in hardware, software, or a combination thereof In the context of software, the blocks represent computer instructions that, when executed by one or more processors, perform the recited operations. For purposes of discussion, the process 200 is described with reference to the components of the exemplary environment 100 described above with reference to FIG. 1.

At block 202, the dynamic wave generator 128 is activated to transmit signals to the FIF probe 116. For example, the dynamic wave generator 128 may transmit signals to the LF transducer 122 included in the FIF probe 116. At block 204, the low frequency transducer 122 may apply the dynamic stress waves 124 to the material 102, 104 proximate the fastener 106.

At block 206, the high frequency UT transducer 118 interrogates the fastener 106 by transmitting and receiving the ultrasonic signals 120. To ensure that the ultrasonic signals 120 pass through the first material 102 and into the second material 104, the interface between the materials 102, 104 typically includes an adhesive, filler, or other material that maintains the stress waves. At block 208, the ultrasonic pulse receiver 130 obtains the ultrasonic signal 120. The process 200 continues at block 210 where the measured phase shift of the signal 120 is correlated to the radial stresses on the fastener 106. The radial stresses are converted and analyzed to determine the interference fit between the fastener 106 and the materials 102, 104 at block 212. For example, the conversion may be configured to trigger an indication to a user whether the measured fastener has an interference fit within the design tolerance, thus indicating the fastener 106 is situated to properly withstand a lightning strike with adequate current dissipation into the surrounding material, provided the material can conduct electricity.

Figure 3:
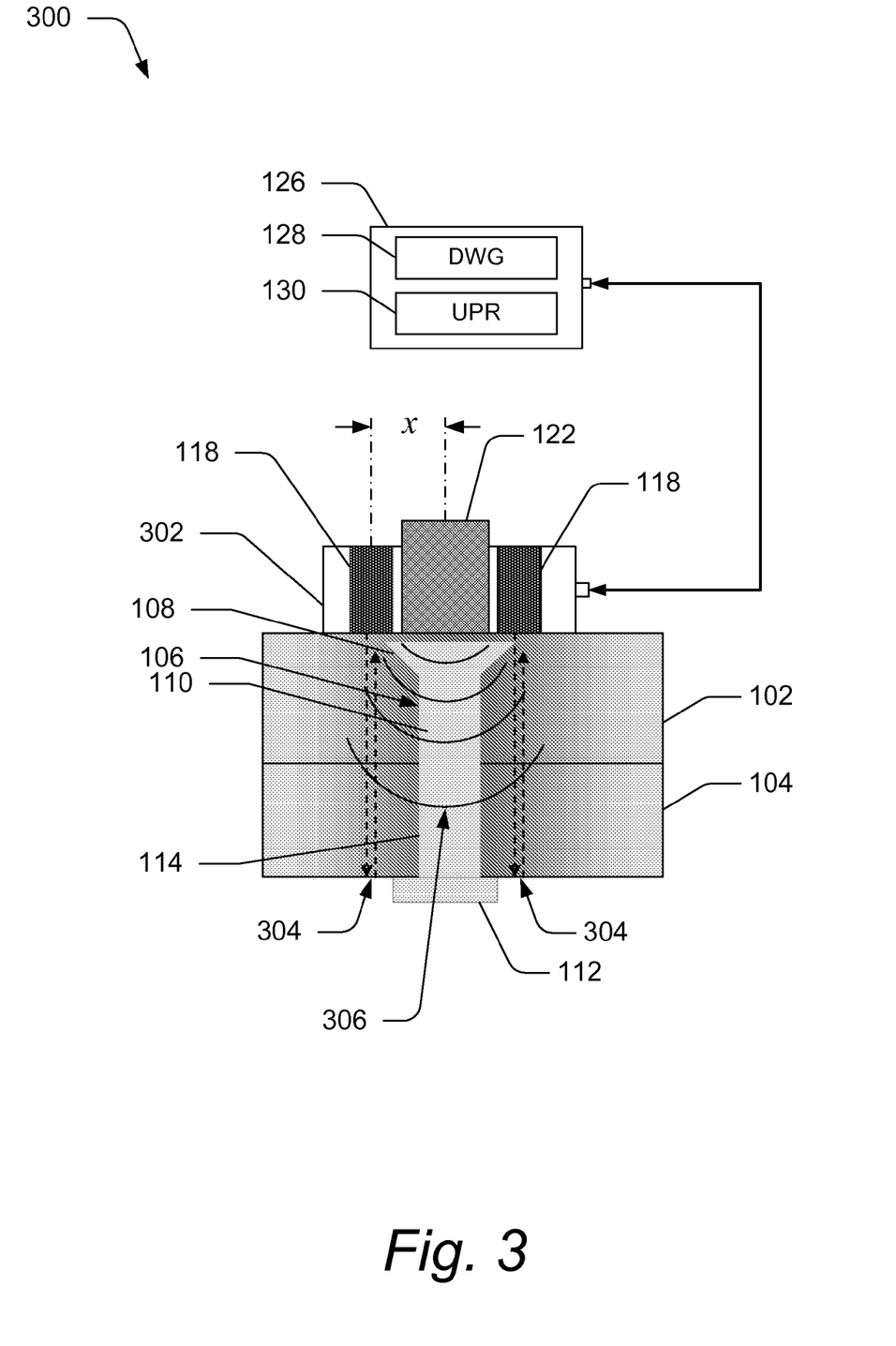
FIG. 3 is a cross-sectional view of another apparatus configured to verify the interference fit of a fastener in accordance with an embodiment of the disclosure.

FIG. 3 is a cross-sectional view of another apparatus configured to verify the interference fit of a fastener in accordance with an embodiment of the disclosure. An environment 300 includes similar hardware as illustrated in the environment 100 in FIG. 1. However, the configuration of the hardware is different in the environment 300, as described more fully below.

A FIF probe 302 includes the HFUT transducer 118 and the LF transducer 122. As illustrated in FIG. 3, the FIF probe 302 may contain more than one HFUT transducer 118, as will be explained below in further detail. The LF transducer 122 produces dynamic stress waves 306 traveling substantially along an axis of the fastener shank 106. In addition, the FIF probe 302 also includes the HFUT transducers 118 for creating ultrasonic signals 304. The HFUT transducers 118 may be mounted adjacent to the LF transducer 122, such that the LF transducer 122 is proximate the fastener 106 and each HFUT transducer 118 is proximate the first material 102.

In operation, the FIF probe 302, via the HFUT transducers 118, interrogates the edge of the fastener 106 to measure the radial (hoop) stress level at a known distance x from the center line. If the stresses around the fastener 106 at the pre-selected distance x are above a threshold, than the interference fit is adequate. If the radial stress is outside the threshold range at any point around the fastener 106, then the interference fit is deemed inadequate.

Figure 4:
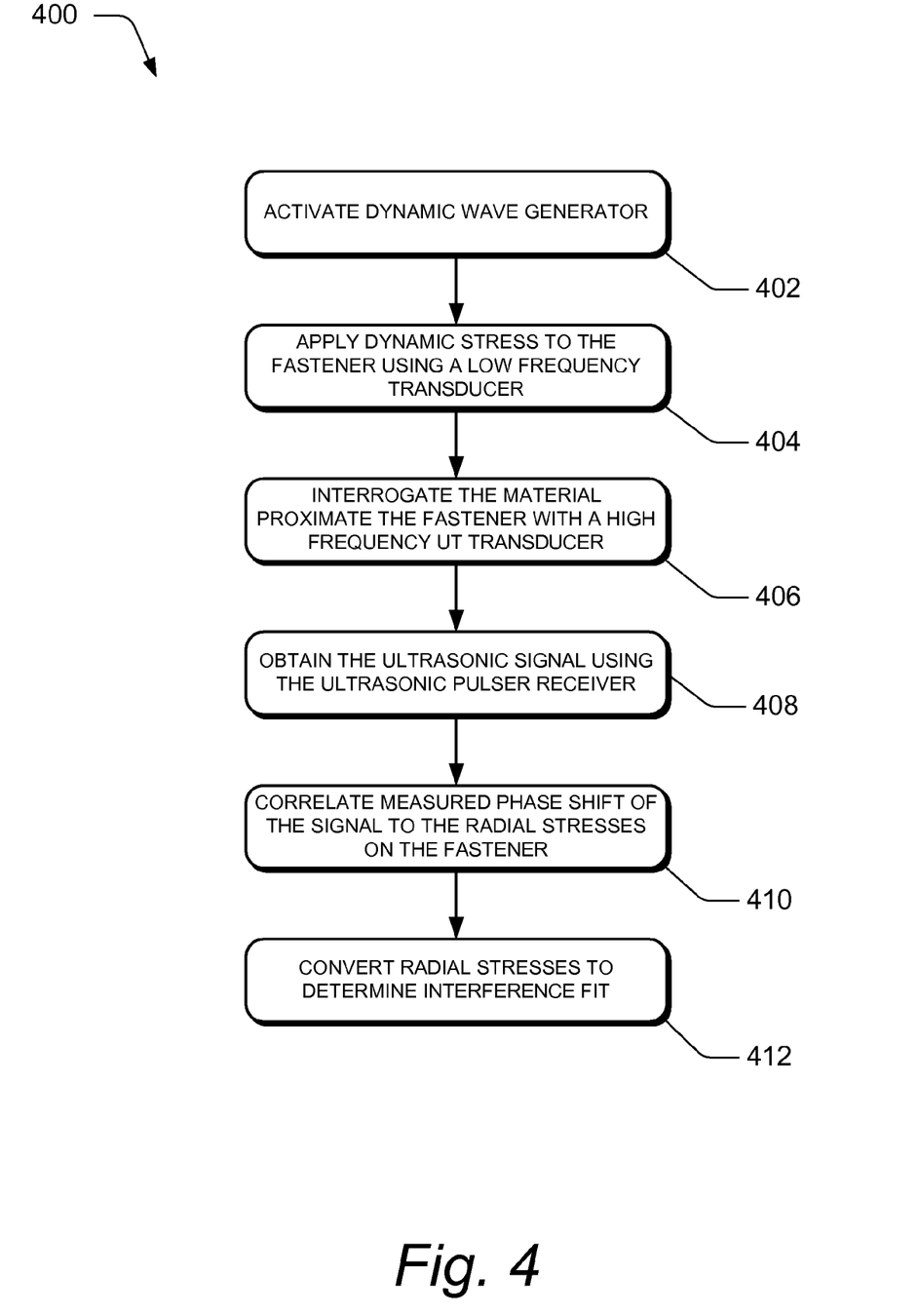
FIG. 4 is a flow diagram of another process for verifying the interference fit of a fastener in accordance with an embodiment of the disclosure.

FIG. 4 is a flow diagram of another process 400 for verifying the interference fit of a fastener in accordance with an embodiment of the disclosure. At block 402, the dynamic wave generator 128 is activated to transmit signals to the FIF probe 302. At block 404, the low frequency transducer 122 may apply dynamic stress to the fastener 106. At block 406, the high frequency UT transducer 118 interrogates the first and second materials 102, 104 proximate the fastener 106 by transmitting and receiving ultrasonic signals 120 at a known distance x from the centerline of the fastener 106. At block 408, the ultrasonic pulser receiver 130 obtains the ultrasonic signal 120.

The process 400 continues at block 410 where the measured phase shift of the ultrasonic signals 120 is correlated to the radial stresses on the fastener 106. The radial stresses are converted to determine the interference fit between the fastener 106 and the materials 102, 104 at block 412. For example, the conversion may be configured to display an interference fit value, such as the calculated value of the actual interference fit between the fastener 106 and the materials 102, 104. The calculated interference fit value may then be used to determine if the fastener 106 meets a design requirement as thus is expected to properly withstand a lightning strike with adequate current dissipation.

Illustrative Interference Fit Measurement

Figure 5:
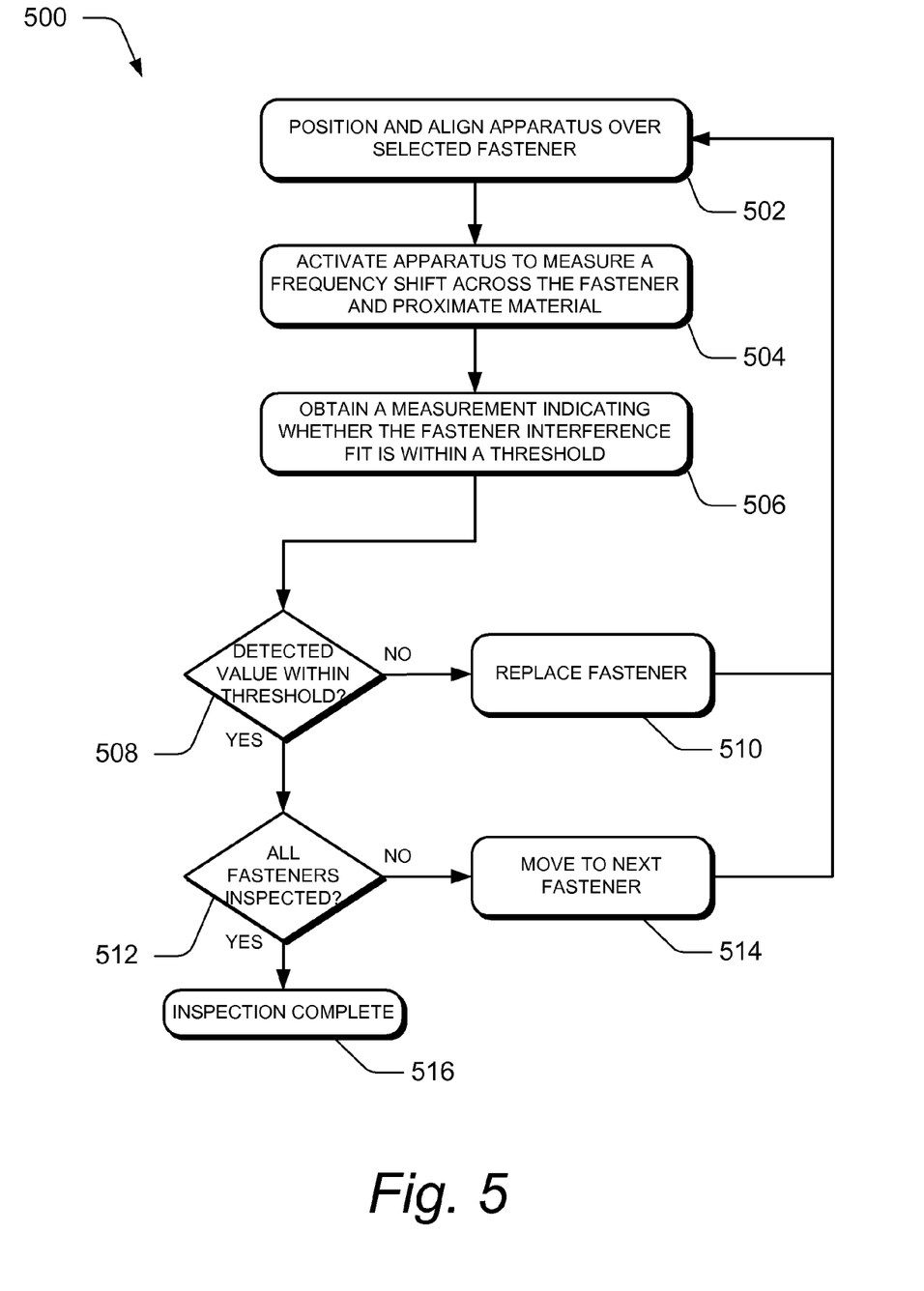
FIG. 5 is a flow diagram of yet another process for verifying the interference fit of a fastener in accordance with an embodiment of the disclosure.

FIG. 5 is a flow diagram of a process 500 for verifying the interference fit of a fastener in accordance with an embodiment of the disclosure. At block 502, the apparatus is positioned and/or aligned over a selected fastener for testing the interference fit. For example, the FIF probe 116 may be aligned over the centerline of the fastener 106. At block 504, the apparatus may be activated to measure a frequency shift across the fastener and proximate material. As described above, the frequency shift may be used to determine the interference fit of the fastener 106 and the material 102, 104. At block 506, the measurement is obtained that indicates whether the interference fit is within an acceptable range or threshold range (e.g., equal to or between a lower threshold and an upper threshold).

At decision block 508, a determination is made whether the interference fit is within the threshold range. If the interference fit is not within the threshold range, the process 500 moves to block 510 and the fastener is replaced. The process 500 continues to the block 502 where the replacement fastener is tested using the process 500 described herein. If the interference fit is determined to be within the threshold range at the decision block 508, the process 500 moves to block 512. At the block 512, a determination is made whether all fasteners have been inspected. If there are more fasteners to inspect, the process 500 continues at block 514 and the next fastener is tested beginning at the block 502. If there are no more fasteners to test, the inspection is complete at block 516.

In some instances, the fasteners 106 may be tested after installation, such as after the fasteners are initially used to secure materials or otherwise used in a manufacturing process. In other instances, the fasteners 106 may be tested after actual use in a particular location. For example, the fastener 106 used to constrain two materials in a wing of an aircraft may be tested with the FIF probe 302 every month, year, or other duration of time to ensure the interference fit is within the threshold range.

The process 500 may also include additional testing of the interference fit for verification or other purposes. For example, the FIF probe 302 may include two HFUT transducers 118. Each transducer may measure the interference fit separately, thus creating two or more measurements for determining if the interference fit is within the threshold range. As illustrated in FIG. 3, two or more transducers may be situated adjacent to the LF transducer 122. In some instances, the distance from one or more HFUT transducer 118 may be more or less than the distance x, thus allowing measurement of the interference fit from different locations within the materials 102, 104.

Figure 6:
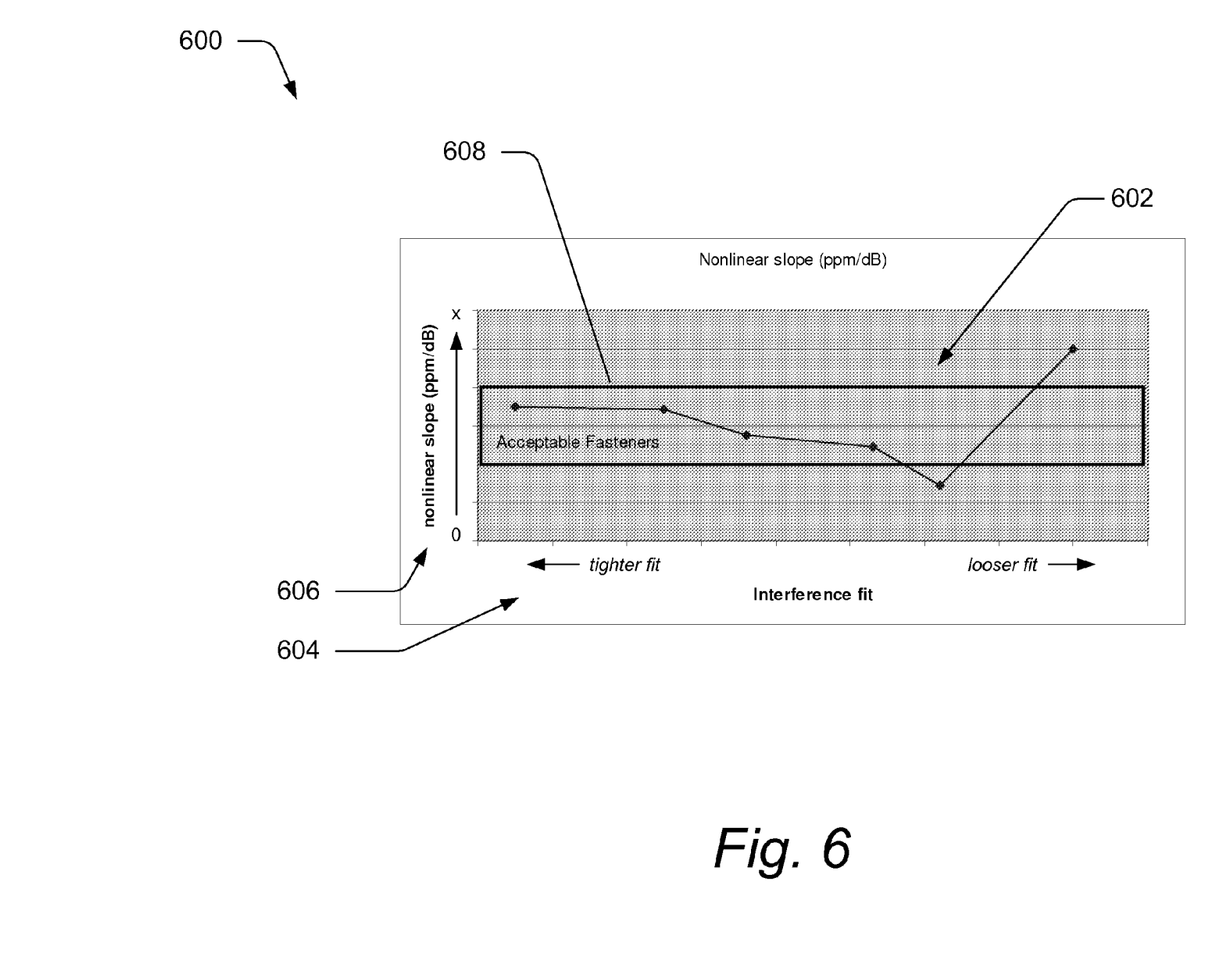
FIG. 6 is a chart illustrating the interference fit of a number of data samples in accordance with an embodiment of the disclosure.

FIG. 6 is an exemplary chart 600 illustrating the interference fit of a number of data samples in accordance with an embodiment of the disclosure. The chart 600 includes a number of test data samples 602, each having a known interference fit 604. A nonlinear slope (ppm/dB) is measured for each test data sample 602 using embodiments of methods and apparatus in accordance with the teachings of the present disclosure.

A correlation process may be used to establish a correlation between observed stresses within the material and the interference fit of the fastener. As illustrated in the exemplary chart 600, a threshold range 608 may be determined for respective interference fits 604 that are within design requirements, thus calibrating the apparatus. For example, the correlation may include correlating empirical (or test) data with the measured stresses. In such an instance, the interference may be known for a number of test samples. The test samples may be analyzed using the techniques and/or apparatus described herein to measure changes in an ultrasonic signal. The measured changes in the ultrasonic signal may then be plotted, associated, or otherwise correlated with the corresponding interference fit of the known sample. In other instances, simulation data may be used with the measured stresses or an analytical expression may be derived from empirical and/or simulation data. In addition, or alternatively, a look-up table may be created to convert a measurement from a signal analysis into a corresponding interference fit.

Each material may have a unique correlation between the observed stresses and the interference fit. For example, a reinforced composite material may have a first associated look-up table (or analytical expression, etc.) while a metallic material may have a second associated look-up table. In addition, different variations of reinforced composite materials may include unique look-up tables to establish the associated corresponding interference fit from a signal analysis.

To test a fastener, the correlation process described above may be reversed once the threshold range is established. Thus, instead of testing a known interference fit with an unknown correlated stress signal, the process may include testing an unknown interference fit using a known correlated stress signal. In such a process, the FIF probe, such as FIF probe 116, may be placed over a fastener and activated. The nonlinear slope measured from the HFUT transducer signal may be compared to the threshold range to determine if the fastener has an acceptable interference fit.

In some embodiments, a local derivative is measured as a function of the applied stress rather than relying on straight measurements of the harmonic amplitudes. A nonlinear response curve includes derivatives that are different depending on the level of the applied stress or remaining residual stress. In order to examine the nonlinear properties of the first and second materials 102, 104 around the fasteners 106 (e.g., fiber reinforced composite material), a test frequency may be established to detect the back echo from the materials. In some instances, a back echo has a frequency of substantially equal to or between 0.5 MHz to 10 MHz. In one instance, a frequency of 2.25 MHz may be ideal for a fiber reinforced composite material surrounding the fastener 106. In the present discussion, it is understood that the term "fiber reinforced composite material" or "reinforced composite material" includes various polymer-based and non-polymeric based materials, commonly referred to as "reinforced composites", "carbon-fiber composites", or still other terms known in the art.

In addition, when the FIF probe 302 is configured as illustrated in FIG. 3, the HFUT transducer 118 may be aligned to slightly overlap the fastener head 108, such as without limitation by 5 mm. An inspection of the slope of the velocity change as a function of the change in intensity may provide a change as a function of a driving amplitude change, which is a measure of the nonlinear parameter. The chart 600 illustrates exemplary sample data points 602 plotted using the aforementioned techniques.

Figure 7:
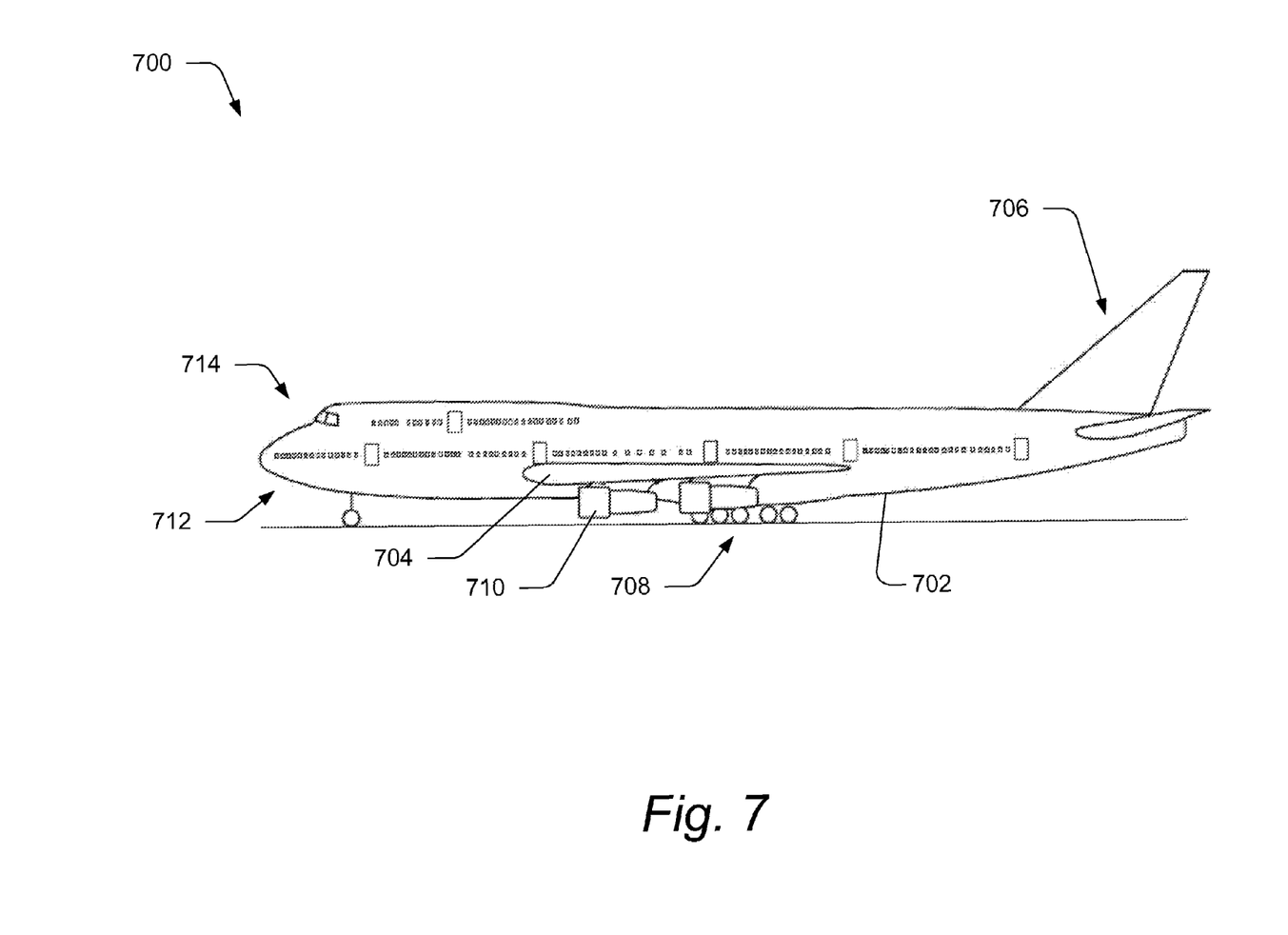
FIG. 7 is a side elevational view of an aircraft having interference fit fasteners verified in accordance with another embodiment of the disclosure.

FIG. 7 is a side elevational view of an aircraft 700 having interference fit fasteners verified in accordance with another embodiment of the disclosure. One may appreciate that fasteners may be employed in a wide variety of locations, including the fuselage, wings, empennage, body, and walls of the aircraft 700. In alternate embodiments, interference fit fasteners may be verified on other types of structures, vehicles, and platforms, such as motor vehicles, aircraft, maritime vessels, or spacecraft, or other suitable applications. For example, the aircraft 700 may include many fasteners throughout the skin of the aircraft in accordance with an embodiment of the disclosure.

In this embodiment, the aircraft 700 includes a fuselage 702 including wing assemblies 704, a tail assembly 706, and a landing assembly 708. The aircraft 700 further includes one or more propulsion units 710, a control system 712 (not visible), and a host of other systems and subsystems that enable proper operation of the aircraft 700. One should appreciate that fasteners may be employed in any suitable portion of the aircraft 700, such as in a fuselage 702 (770*a*), wing assemblies 704 (770*b*), tail assembly 706 (770*c*), and any other suitable areas of the aircraft 700. In general, the various components and subsystems of the aircraft 700 may be of known construction and, for the sake of brevity, will not be described in detail herein.

Although the aircraft 700 shown in FIG. 7 is generally representative of a commercial passenger aircraft, including, for example, the 737, 747, 757, 767, 777, and 787 models commercially available from The Boeing Company of Chicago, Ill., the inventive apparatus and methods disclosed herein may also be employed in the assembly of virtually any other types of aircraft. More specifically, the teachings of the present disclosure may be applied to the manufacture and assembly of other passenger aircraft, fighter aircraft, cargo aircraft, rotary aircraft, and any other types of manned or unmanned aircraft, including those described, for example, in The Illustrated Encyclopedia of Military Aircraft by Enzo Angelucci, published by Book Sales Publishers, September 2001, and in Jane's All the World's Aircraft published by Jane's Information Group of Coulsdon, Surrey, United Kingdom, which texts are incorporated herein by reference.

CONCLUSION

While preferred and alternate embodiments of the disclosure have been illustrated and described, as noted above, many changes can be made without departing from the spirit and scope of the disclosure. Accordingly, the scope of the disclosure is not limited by the disclosure of these preferred and alternate embodiments. Instead, the disclosure should be determined entirely by reference to the claims that follow.

What is claimed is:

1. A method of determining an interference fit of a fastener, comprising:
    transmitting a low frequency stress wave through a first portion of a structure, the structure including a material secured with a fastener;
    monitoring an ultrasonic signal transmitted through a second portion of the structure, the second portion being separated from the first portion by an interference portion defined between the fastener and the material;
    measuring a phase shift from the ultrasonic signal; and
    determining an interference fit from the measured phase shift.

2. The method of claim 1, wherein the first portion is proximate the fastener and the second portion is proximate the material.

3. The method of claim 1, wherein determining an interference fit from the measured phase shift of the ultrasonic signal includes comparing the measured phase shift to a threshold value.

4. The method of claim 1, wherein the ultrasonic signal is generated by a high frequency ultrasonic testing (HFUT) transducer.

5. The method of claim 4, wherein the HFUT transducer generates a back echo with a frequency of substantially equal to or between 0.5 MHz to 10 MHz.

6. The method of claim 1, wherein measuring the phase shift from the ultrasonic signal includes measuring the ultrasonic signal with an ultrasonic pulser receiver.

7. The method of claim 1, wherein the first portion is proximate the material and the second portion is proximate the fastener.

8. A method of verifying an interference fit, comprising:
    aligning a probe to a fastener;
    activating the probe, the probe transmitting low frequency stress waves into a first portion of a structure and measuring the stress waves with an ultrasonic signal at a second portion of the structure, the first and second portions of the structure being separated by an interference between a fastener and a material proximate the fastener;
    calculating an interference fit between the fastener and the material from the measured stress waves; and
    determining if the interference fit is within a threshold range.

9. The method of claim 8, wherein the first portion is proximate the material and the second portion is proximate the fastener.

10. The method of claim 8, wherein activating the probe includes activating a low frequency transducer to generate low frequency stress waves and activating a high frequency ultrasonic testing (HFUT) transducer to generate high frequency ultrasonic signals.

11. The method of claim 8, wherein calculating the interference fit between the fastener and the material includes outputting a value for the interference fit.

12. The method of claim 8, wherein the fastener includes a straight shank, a head, and a threaded portion to receive a bolt.

13. The method of claim 8, wherein the material is fiber reinforced composite material.

14. A method, comprising:
    aligning a probe proximate a fastener that is disposed within a material, the fastener having an longitudinal axis;
    generating stress waves from the probe using a low frequency transducer, the stress waves being directed substantially parallel to the longitudinal axis;
    generating ultrasonic signals from the probe using a high frequency ultrasonic testing (HFUT) transducer, the HFUT to transmit ultrasonic signals being directed substantially parallel to the longitudinal axis, the stress waves to create a phase shift or velocity shift of the ultrasonic signals when the stress waves pass between the fastener and the material;
    interrogating the ultrasonic signals with an ultrasonic pulse receiver after the stress waves pass between the fastener and the material; and
    determining an interference fit parameter between the fastener and the material based on the measurement of the ultrasonic signal interrogated by the ultrasonic pulse receiver.

15. The method of claim 14, wherein generating the stress waves using a low frequency transducer includes generating dynamic stress waves using a dynamic wave generator.

16. The method of claim 14, wherein determining the interference fit includes determining at least one of a phase shift and a velocity shift of the ultrasonic signals generated by the HFUT transducer.

17. The method at claim 14, wherein determining an interference fit based on the interrogated stress signal includes comparing the interrogated stress signal to a threshold value.

18. The method of claim 14, wherein the low frequency transducer is a ring transducer configured to produce uniform stress waves around the fastener.

* * * * *